United States Patent [19]

Fukui et al.

[11] Patent Number: 4,898,466

[45] Date of Patent: Feb. 6, 1990

[54] METHOD AND APPARATUS FOR EMISSION SPECTROSCOPIC ANALYSIS

[75] Inventors: Isao Fukui, Uji; Shuzo Hayahsi, Kyoto; Takao Miyama, Muko, all of Japan

[73] Assignee: Shimadzu Corporation, Japan

[21] Appl. No.: 274,332

[22] Filed: Nov. 21, 1988

[30] Foreign Application Priority Data

Nov. 30, 1987 [JP] Japan .................................. 62-303988
Apr. 26, 1988 [JP] Japan .................................. 63-103167

[51] Int. Cl.$^4$ ...................... G01N 21/63; G01N 21/67
[52] U.S. Cl. ...................................... 356/313; 356/318
[58] Field of Search .................................. 356/313, 318

[56] References Cited

U.S. PATENT DOCUMENTS 3,680,959  8/1972  Schuch ................................ 356/318
4,641,968  2/1987  Grandy ............................... 356/313

Primary Examiner—F. L. Evans
Attorney, Agent, or Firm—Fidelman & Wolffe

[57] ABSTRACT

Method and apparatus for emisson spectroscopic analysis by spark discharge, wherein each and every one of a number of spark discharges conducted for analysis of a sample comprises a high energy portion providing a sufficient amount of energy to vaporize the elements contained in the sample and a low energy portion providing a sufficient amount of energy to cause the vaporized elements to emit light, and wherein spectroscopic measurement is conducted in the low energy portion, or initiated in the end portion of high energy portion to continue in the low energy portion.

19 Claims, 4 Drawing Sheets

METHOD AND APPARATUS FOR EMISSION SPECTROSCOPIC ANALYSIS

BACKGROUND OF THE INVENTION

This invention relates generally to emission spectroscopy and more particularly to a method and an apparatus for emission spectroscopic analysis which utilizes spark discharge.

In emission spectroscopic analysis using spark discharge, it is customary to pretreat the surface of a sample to be analyzed by applying spark discharges to the sample surface before analysis is conducted so as to reduce the adverse influence of small scars and/or pinholes on or in the sample surface and/or foreign matters attached thereto on the results of analysis, thereby improving the accuracy of analysis. The pretreatment requires high-energy spark discharges conducted for more than 10 seconds in order to conduct an analysis for 5 seconds. The spark discharges for pretreatment of a sample will be referred to as the "preparatory discharges". The more preparatory discharges are conducted, the higher the accuracy of analysis becomes. After a sufficient number of preparatory discharges have been applied to a sample surface, spark discharges for analysis are applied to the sample surface pretreated by the preparatory discharges. The discharges for analysis will be referred to as the "analytic discharges".

The reason why the time required for preparatory discharges is longer than the time required for analytic discharges is that the position in the surface of a sample which is struck by each of the spark discharges produced in one operation of analysis is uncertain, so that the whole area of the sample surface must be treated beforehand by preparatory discharges. The more accurate an analysis is to be made, the longer period of time the preparatory discharges require.

Accordingly, the primary object of the invention is to provide a method and an apparatus for emission spectroscopy analysis which utilize spark discharge as a light source and which are capable of not only shortening the time required for analysis substantially as compared with the conventional methods and instruments but also materially improving the accuracy of analysis.

The analytic discharge is conducted with high energy, so that it is highly capable of vaporizing a sample. The resulting background light, however, is strong as compared with the emission lines of the component elements of the sample, with resulting decrease in the accuracy off analysis. Therefore, low-energy discharge is suitable for analysis itself.

If the energy for analytic discharge is too low, however, the amount of the sample components vaporized decreases and the intensity of the light of the spectral emission lines produced becomes weak, with resulting reduction of the sensitivity and accuracy of analysis. Therefore, a sufficient amount of the sample must be vaporized by analytic discharges so that there is a limit to which the energy level of the analytic discharges can be lowered, with resulting difficulty in reducing the background light.

Accordingly, another object of the invention is to provide a method and an apparatus for emission spectroscopic analysis which utilize spark discharge as a light source and which are capable of reducing the amount of energy for analytic discharge while simultaneously improving the accuracy and sensitivity of analysis.

SUMMARY OF THE INVENTION

Briefly stated, the invention provides a method of emission spectroscopic analysis of a sample containing elements to be analyzed, which comprises: providing energy in the form of cyclic pulses each having a waveform which comprises a relatively high energy portion and a relatively low energy portion continuing from the high-energy portion, the high-energy portion providing a sufficient amount of energy to vaporize the elements contained in the sample and the low-energy portion providing a sufficient amount of energy to cause at least a part of the vaporized elements to emit light; concentrating each of the pulses on the sample; and spectroscopically measuring the light emitted by the vaporized elements.

The relatively high energy must be provided by either spark discharge or laser while the relatively low energy is provided by spark discharge.

The high-energy portion of the above-mentioned waveform includes a first relatively high peak which comes first in the waveform of each of the pulses while the low-energy portion continuing from the high-energy portion may comprise a second peak which is lower than the first peak. The low-energy portion may further include a third peak whichis lower than the second peak and follows the second peak.

The light measuring step may be taken to measure only the light emitted by the vaporized sample in the low-energy portion of each of the pulses. In case the low-energy portion includes a second and a third peak, the energy provided by either of these two peaks may selectively be used in accordance with the kinds of the elements contained in the sample to be analyzed.

The energy provided by the high-energy portion of each spark discharge and applied to the sample vaporizes a portion of the sample and the vapor produced contains impurities attached to the surface of the sample as well as the elements contained in the sample. As the vaporization of the sample proceeds in the high-energy portion, the vapor previously produced is dissipated so as to be replaced by new vapor continuously supplied from the sample, and the vapor produced in the end portion of the high-energy portion contains a negligible amount of impurities, if any. Therefore, the step of measuring the light emitted by the vapor may be started in the end portion of the high-energy portion of each pulse applied to the sample before the suceeding low-energy portion thereof is reached. In other words, the light-measuring step may be started while the sample vapor produced adjacent the end of the high-energy portion and containing little or no impurities remains there so that it is possible to measure the light emitted by the above-mentioned vapor as well as the vapor produced in the low-energy portion.

The invention also provides an apparatus for emission spectroscopic analysis of a sample containing elements to be analyzed, which comprises: means for providing energy in the form of cyclic pulses each having a waveform which comprises a relatively high energy portion which provides a sufficient amount of energy to vaporize the elements contained in the sample and a relatively low energy portion which continues from the high-energy portion and provides a sufficient amount of energy to cause the vaporized elements to emit light, and concentrating the energy of each of the pulses on the sample; means for spectroscopically measuring the light emitted by the vaporized elements; and means for controlling the light measuring means so that the light measuring means measures the light emitted by the vapor a predetermined period of time after the beginning of the high-energy portion of each of the pulses.

The above-mentioned energy providing and concentrating means can use spark discharge as the energy to vaporize a sample and cause the sample vapor to emit light. Alternatively, the energy providing and concentrating means may comprise a combination of a laser which produces a laser beam to be concentrated onto a required area of a sample to vaporize it and a spark generator to generate a spark to cause the sample vapor to emit light.

In case spark discharge is used as the energy source, the high-energy portion of the waveform of each of the pulses produced by the above-mentioned energy providing means corresponds to the preparatory discharge, and the low-energy portion of the waveform corresponds to the analytic discharge.

The above-mentioned controlling means may control the light measuring means so that the latter means measures the light emitted by the vapor only in the low-energy portion of the waveform. The controlling means may also control the light measuring means so that the latter means measures the light emitted by the vapor in the end portion of the high-energy portion as well as in the low-energy portion.

The characteristic of the invention is that each and every excitation of a sample consists of a first step of vaporizing the sample and a second step of analyzing the vaporized sample, the second step being taken continuously from the first step. In the conventional methods, many preparatory discharges are conducted at a high-energy level to treat the whole area of a sample where sparks are expected to occur in subsequent analytic discharges, which are conducted at a comparatively low energy level, so that the preparatory discharges require a long time. Moreover, it is practically difficult to treat the whole area by the preparatory discharges so that there must be in the area some places left untreated, with resulting reduction of the accuracy of analysis.

In accordance with the invention, at each and every one of a number of spark discharges conducted for one operation of analysis of a sample, a first step of vaporizing the sample is continuously succeeded by a second step of analyzing the vaporized sample, with an amount of energy suitable for each of the steps. Generally, a spark remains at substantially the same point while it continues. This causes an analytic spark discharge to take place on that spot on the surface of the sample that has been cleaned by a preparatory discharge. Therefore, immediately before an analytic spark discharge is conducted, that spot on the sample surface which is to be analyzed has only to be treated by a preparatory discharge at a high energy level.

With the above-mentioned arrangement of the invention, it is not necessary to spend for preparatory discharges such a long time as in the conventional methods, and it seldom happens that a spark strikes that part of the surface area of a sample which is left untreated by a preparatory spark discharge, with resulting deterioration of the accuracy of analysis.

As previously mentioned, in the prior art methods analytic spark discharges are conducted with comparatively low energy after preparatory spark discharges are conducted with comparatively high energy. Although it is desirable for analytic spark discharges to be conducted with as low energy as possible, they must provide a sufficient amount of energy to enable vaporization of the sample. If the amount of energy is too small, the intensity of the spectral emission lines of the sample components becomes weakened with resulting lowering of the sensitivity and accuracy of analysis. Therefore, the energy level of the analytic spark discharges must be high enough to produce emission lines of the sample components having a sufficient intensity, with resulting increase in noise signal caused by background light.

In accordance with the invention, at each spark discharge the sample is vaporized by high energy, and while the sample vapor remains, the vapor is analyzed. This makes it unnecessary for analytic spark discharges to vaporize as much of the sample as would otherwise be necessary, and a low energy suffices for analysis provided that it can produce spectral emission lines of a sufficient light intensity, so that the background level is lowered and the minimum concentration of the sample required for quantitative analysis is reduced. In other words, high sensitivity and accuracy can be obtained in analysis.

PREFERRED EMBODIMENTS OF THE INVENTION

Figure 1:
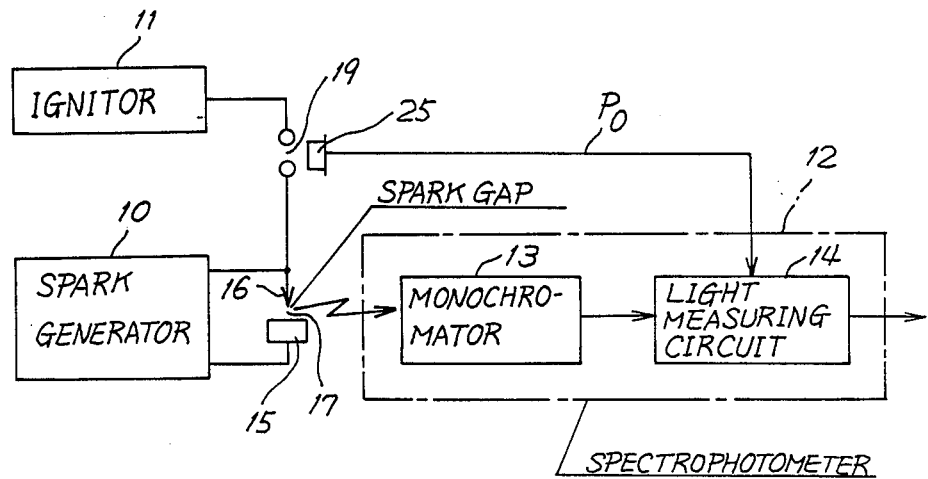
FIG. 1 is a block diagram schematically showing one embodiment of the invention.

FIG. 1 schematically shows one embodiment of the invention which comprises a spark generator 10, an ignitor 11, and a spectrophotometer 12 which comprises a monochromator 13 and a light measuring circuit 14. A sample 15 to be analyzed and an electrode 16 are juxtaposed across a spark gap 17 in which a spark discharge is generated as will be described hereinbelow.

Figure 2:
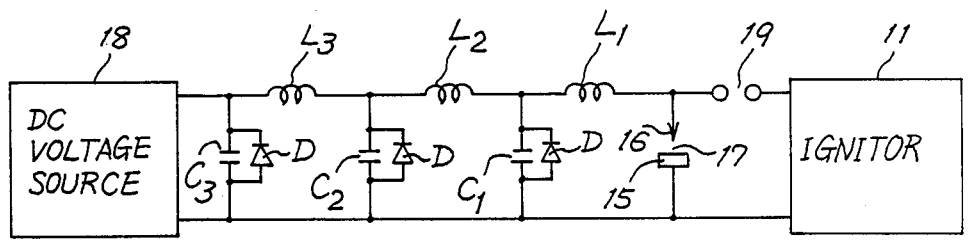
FIG. 2 is an electrical circuit diagram of a portion of FIG. 1.

FIG. 2 shows a concentrate arrangement of the spark generator 10 which comprises capacitors $C_1$, $C_2$ and $C_3$ with a protective diode D connected across each of the capacitors, inductors $L_1$, $L_2$ and $L_3$ and a direct current source 18 which charges the capacitors. The capacitance of the capacitor $C_1$ is greater than those of the capacitors $C_2$ and $C_3$. The spark gap 17 is connected in parallel with the capacitors, and the ignitor 11 is connected across the spark gap 17 through an ignition gap 19. When the ignitor 11 produces a high-voltage pulse to render the ignition gap 19 conducting, the spark gap 17 is rendered conducting, whereupon the charge stored in the capacitors $C_1$, $C_2$ and $C_3$ are successively discharged through the inductors $L_1$, $(L_1+L_2)$ and $(L_1+L_2+L_3)$, respectively. The protective diodes D function to prevent the L-C circuits from oscillating.

Figure 3A:
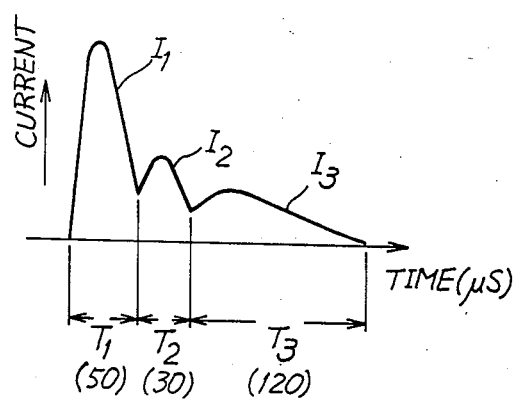
FIG. 3A is a waveform diagram for explanation of the operation of the apparatus shown in FIG. 1.

FIG. 3(A) shows the waveforms of the discharge currents $I_1$, $I_2$ and $I_3$ provided by the capacitors $C_1$, $C_2$ and $C_3$, respectively. The discharge current $I_1$ from the capacitor $C_1$ passes through the inductor $L_1$ only, so that it has the highest peak with a small pulse width and provides the greatest amount of energy. The discharge current $I_2$ from the capacitor $C_2$ passes through the two inductors $L_1$ and $L_2$, so that it has a peak lower and less steep than the highest peak and provides a smaller amount of energy than the current $I_1$. The discharge current $I_3$ from the capacitor $C_3$ passes through all of the three inductors $L_1$, $L_2$ and $L_3$, so that it has the lowest peak whichis far less steep and provides the smallest amount of energy. The discharges of the currents $I_1$, $I_2$ and $I_3$ are referred to as the high-energy discharge, the normal spark discharge and the arc-like spark discharge, respectively. While the high-energy discharge is used for the previously mentioned preparatory discharge, the normal spark discharge and the arc-like spark discharge are selectively used for the analytic spark discharge depending upon the kind of the elements to be analyzed. Either one of the normal and arc-like spark discharges may be selected in accordance with the kind of sample and the purpose of analysis, or both of the discharges may be used to conduct two types of analyses continuously. The periods of time $T_1$, $T_2$ and $T_3$ of duration of the spark discharges with the currents $I_1$, $I_2$ and $I_3$, respectively, may be about 50 $\mu$s, 30 $\mu$s, and 120 $\mu$s, respectively, for example.

Figure 3B:
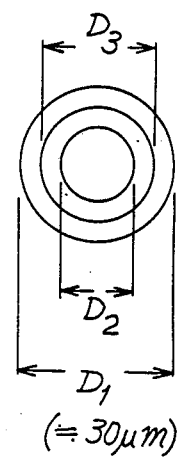
FIG. 3B schematically shows the marks which spark discharges leave on the surface of a sample being analyzed.

FIG. 3(B) schematically shows the marks caused by the different spark discharges on the sample surface. The mark caused by the high-energy discharge has the greatest diameter $D_1$ of about 30 $\mu$m, and the mark caused by the arc-like discharge has a smaller diameter $D_3$ and the mark caused by the normal spark discharge has the smallest diameter $D_2$.

The spark discharges with the currents $I_1$, $I_2$ and $I_3$, respectively, may be considered as component parts of a single spark discharge or pulse comprising a relatively high energy portion providing the current $I_1$ and a relatively low energy portion providing the currents $I_2$ and $I_3$. The frequency of the pulse or spark discharge is preferably 400 times per second, and one operation of analysis requires about 200 pulses or spark discharges, which take about 5 seconds.

Figure 4:
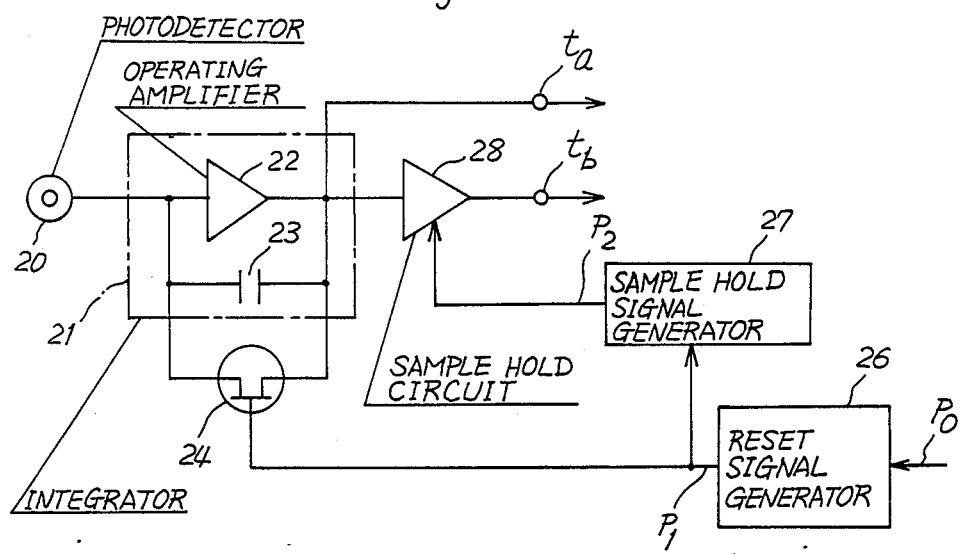
FIG. 4 is an electrical circuit diagram of a portion of the apparatus shown in FIG. 1.

In order to measure the light caused by the low-energy normal spark discharge and/or the arc-like spark discharge, a control circuit as shown in FIG. 4 is connected to the input portion of the light measuring circuit 34 of the spectrophotometer 12.

Figure 5:
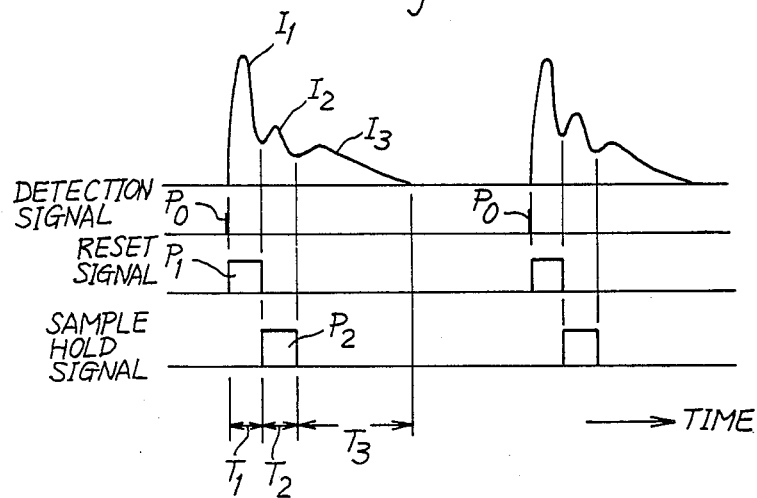
FIG. 5 is a waveform diagram for explanation of the operation of the circuit shown in FIG. 4.

The monochromatic light emerging from the monochromator 13 is received by a photodetector 20, which converts the light signal to a corresponding electrical signal. The electrical signal is integrated by an integrator 21 comprising an operational amplifier 22 and a capacitor 23, with a reset switch 24 connected across the capacitor 23. In particular, when the ignitor 11 produces a high-voltage ignition signal to cause a spark discharge to occur in the ignition gap 19 in FIG. 1, a photodetector 25 detects the ignition signal to produce a detection signal $P_0$, which causes a reset signal generator 26 in the form of a one-shot multivibrator to produce a reset pulse signal $P_1$ having a variable pulse width which may be set to the duration $T_1$ of the high-energy discharge current $I_1$, as shown in FIG. 5. The pulse signal $P_1$ makes the reset switch 24 conducting, thereby to short-circuit the capacitor 23 for the period of time $T_1$ for the high-energy spark discharge, so that the integrator 21 does not integrate the output from the photodetector 20 caused by the preparatory discharge current $I_1$. At the end of the period of time $T_1$ the switch 24 becomes nonconducting, so that the integrator 21 begins to integrate the signal from the photodetector 20 caused by the normal spark discharge current $I_2$.

When the switch 24 is rendered nonconducting upon disappearance of the pulse $P_1$ or passage of the period of time $T_1$, the vapor of the sample produced by the high-energy discharge and containing little or no impurities remains in the discharge gap 17 for a while, so that the integrator 21 integrates the output signal from the photodetector 20 caused by the light emitted from the above-mentioned remaining sample vapor by the normal spark discharge. If the width of the pulse $P_1$ is changed, the amount of the above-mentioned remaining vapor changes.

On the other hand, a sample hold signal generator 27 in the form of a one-shot multivibrator responds to the descending edge of the reset signal $P_1$ to produce a sample hold signal $P_2$ having a variable pulse width wich may be set to the period of time $T_2$ for the normal spark discharge. The signal $P_2$ is applied to a sample hold circuit 28, and at the end of the period of time $T_2$ the sample hold circut 28 holds the output from the integrator 21, that is, the integrated value of the output signal from the photodetector 20 caused by the normal spark discharge current $I_2$ and produces a corresponding output at a terminal $t_b$.

The integrated value of the output signal from the photodetector 20 caused by both the normal spark discharge current $I_2$ and the arc-like spark discharge current $I_3$, that is, the output of the integrator 21 for the periods of time $T_2$ and $T_3$ is taken out at a terminal $t_a$.

For quantitative determination of an element for which the normal spark discharge is suitable, the output at the terminal $t_b$ caused by the normal spark discharge is to be accumulated for the same number of times as the spark discharges conducted for analysis of a sample, and for quantitative determination of an element for which the arc-like spark discharge is suitable, the signal obtained by subtracting the output at the terminal $t_b$ from the output at the terminal $t_a$ is to be accumulated for the same number of times as the spark discharges.

The following table shows the results of an analysis made by the apparatus of the invention as compared with those made by a conventional method. The sample is steel, and the quantities of carbon C, phosphor P, sulfur S, boron B and lead Pb contained in the sample are determined. In the table "BEC", which indicates the background equivalent concentration, is the concentration of an element that renders 1:1 the ratio between the intensity of the background signal and that of the emission line signal caused by the element to be determined. The smaller the ratio is, the higher the sensitivity of detection is.

TABLE

| ELEMENT | WAVELENGTH (nm) | BEC (%) | | LOWER LIMIT OF QUANTITATIVE DETERMINATION (%) | |
| --- | --- | --- | --- | --- | --- |
| | | PRIOR ART | PRESENT INVENTION | PRIOR ART | PRESENT INVENTION |
| C | 193.0 | 0.040 | 0.015 | 0.0020 | 0.0007 |
| P | 178.2 | 0.025 | 0.0055 | 0.001 | 0.0003 |
| S | 180.7 | 0.015 | 0.0010 | 0.001 | 0.0005 |
| B | 182.6 | 0.0030 | 0.0010 | 0.0002 | 0.0005 |
| Pb | 405.7 | 0.15 | 0.01 | 0.001 | 0.0003 |

Figure 6A:
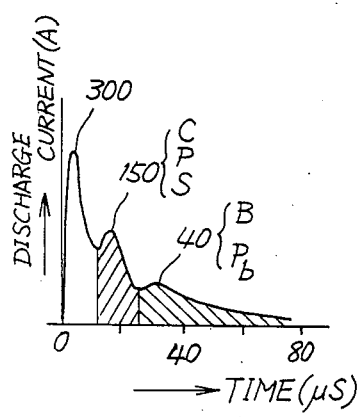
FIG. 6(A) shows a waveform of a triple-peak spark discharge used by the apparatus of the invention for analysis of a sample.
Figure 6B:
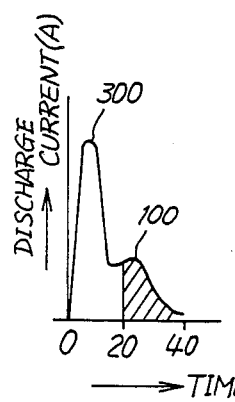
FIGS. 6(B) and 6(C) show the waveforms of different spark discharges which may be used.
Figure 6C:
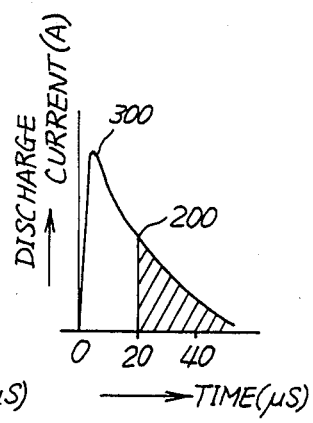

FIGS. 6(A), 6(B) and 6(C) show the waveforms of discharge currents used in one embodiment of the invention. FIG. 6(A) shows the waveform of a triple-peak discharge with which the values given in the above table are obtained. The discharge current value is the peak top current value at each discharge stage. As previously mentioned, the first, second and third peaks are resulted from the preparatory discharge, the normal spark discharge and the arc-like spark discharge, respectively. The elements C, P and S are analyzed with the normal spark discharge and the elements B and Pb are analyzed with the arc-like spark discharge.

FIG. 6(B) shows the waveform of a double-peak discharge current. In this case, one of the three L-C combinations, say, the inductor $L_3$ and the capacitor $C_3$ with its diode D are removed from the circuit shown in FIG. 2.

FIG. 6(C) shows the waveform of a single-peak discharge current. In this case, after a predetermined period of time, say, 20 $\mu$s from the start of the discharge and from a point on the rear descending slope of the waveform, the output from the photodetector 20 in the remaining portion of the waveform is sampled. In this case, two of the L-C circuits, say, the inductors $L_2$, $L_3$ and the capacitors $C_2$, $C_3$ with the two protective diodes D are removed from the circuit of FIG. 2, which then includes the single L-C circuit comprising the inductor $L_1$ and the capacitor $C_1$ with its protective diode D.

In the above embodiments of FIGS. 6(A) and 6(B) the analytic discharge is initiated ten and several $\mu$s after the start of the preparatory discharge. The period of time during which the vapor of the sample produced by the preparatory discharge remains in the discharge gap varies with the kind of the vaporized element within the range of several $\mu$s to a fraction of a second, so that the time $T_1$ from the start of the preparatory discharge to that of the analytical discharge or the pulse width of the reset pulse $P_1$ may be set to a suitable time within the above range.

Figure 7:
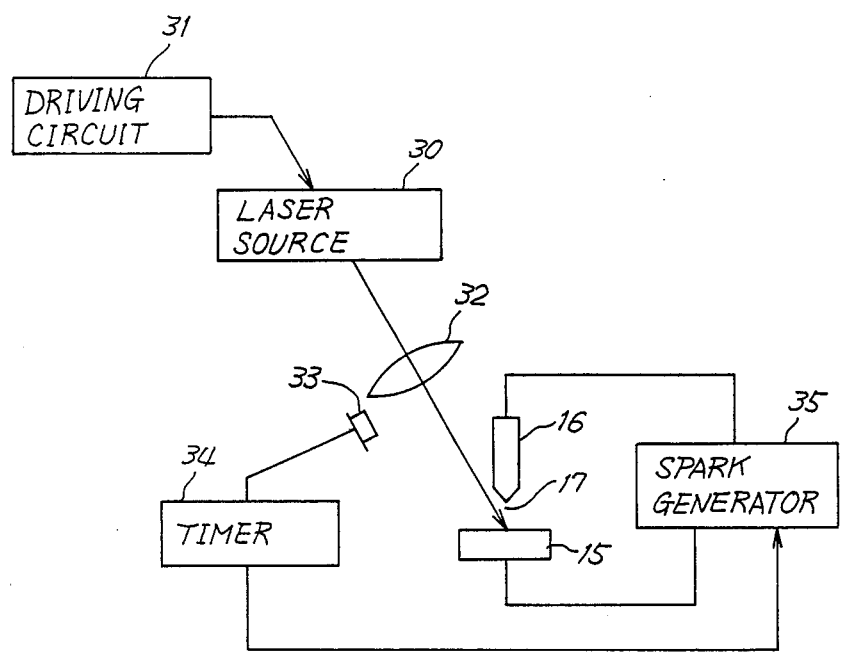
FIG. 7 is a block diagram schematically showing another embodiment of the invention which uses a laser.

The preparatory discharge for vaporizing a sample in the embodiments of FIGS. 6(A) and 6(B) may be replaced by irradiation of the sample with a laser beam. FIG. 7 shows an arrangement in which a laser is used for vaporization of the sample. The apparatus comprises a laser source 30, a circuit 31 for driving the source 30 to produce a pulse of laser beam at a predetermined cycle, and a lense 32 for focusing the laser beam onto a point on the surface of a sample 15, thereby to cause the material of the sample at the point to vaporize. At one side of the laser beam there is provided a beam detector 33 which detects the laser beam to produce a detection signal, which triggers a timer 34. Upon passage of a time $T_1$ preset in the timer, it produces a signal to cause a spark generator 35 to produce an analytic spark discharge in a gap 17 between the sample 15 and an electrode 16. The time $T_1$ set in the timer 34, that is, the timing for starting the analytic discharge, varies with the kinds of the sample and elements to be analyzed within a range of several $\mu$s to a fraction of a second in which the vapor of the elements can remain in the discharge gap 17, and the optimum times for different elements are determined beforehand by experiments.

In accordance with the invention, each and every one of a number of spark discharges conduit for one operation of analysis of a sample comprises a first step of vaporizing the sample by preparatory discharge or laser and a second step of analyzing the sample vapor by analytic spark discharge, and the first step is continuously followed by the second step, so that as compared with the conventional methods wherein preparatory discharges and analytic discharges are conducted separately and independently of each other, the method of the invention requires a shorter period of time. In addition, since the first and second steps are taken at the same spot on the sample, it seldom happens to the method of the invention that an analytic discharge cuases a spark to hit a point on the sample which is not pretreated by any preparatory discharge thereby to deteriorate the accuracy of analysis. In addition, since the first step of vaporizing the sample is immediately followed by the second step of analysing the sample vapor, the sample vapor produced in the first step can be used for analysis, so that the spark discharge in the second step can be conducted with a smaller amount of energy than otherwise, with resulting reduction of the background noise and improvement of the accuracy of analysis.

What we claim is:

1. A method of emission spectroscopic analysis of a sample containing elements to be analyzed, comprising:
    providing energy in the form of a cyclic pulses each having a waveform which comprises a relatively high energy portion and a relatively low energy portion continuing from said relatively high energy portion, said relatively high energy portion providing a sufficient amount of energy to vaporize said elements contained in said sample and said relatively low energy portion providing a sufficient amount of energy to cause said vaporized elements to emit light;
    concentrating the energy of each of said pulses on said sample; and
    spectroscopically measuring said light emitted by said vaporized elements.

2. The method of claim 1, wherein the energy provided by said relatively low energy portion of each of said pulse is provided by spark discharge.

3. The method of claim 2, wherein the energy provided by said relatively high energy portion of each of said pulses is provided by spark discharge.

4. The method of claim 2, wherein the energy provided by said relatively high energy portion of each of said pulses is provided by laser.

5. The method of claim 1, wherein said relatively high energy portion of each of said pulses include a first relatively high peak while said relatively low energy portion includes a second peak which is lower and less steep than said first peak.

6. The method of claim 5, wherein said relatively low energy portion further includes a third peak which is lower and less steep than said second peak and continues from said second peak.

7. The method of claim 1, wherein said measuring step is taken in said relatively low energy portion.

8. The method of claim 1, wherein said measuring step is initiated in the end portion of said relatively high energy portion of each of said pulses, and continues in said relatively low energy portion.

9. A method of emission spectroscopic analysis of a sample containing elements to be analyzed, comprising:
providing energy in the form of cyclic pulses each having a waveform which comprises a relatively high energy portion and a relatively low energy portion continuing from said first portion, said relatively high energy portion providing a sufficient amount of energy to pretreat said sample and said relatively low energy portion providing a sufficient amount of energy to cause the elements contained in said sample to vaporize and simultaneously emit light;
concentrating the energy of each of said pulses on said sample; and
spectroscopically measuring said light emitted by said elements vaporized by said relatively low energy portion.

10. The method of claim 9, wherein the energy provided by said relatively low energy portion of each of said pulses is provided by spark discharge.

11. The method of claim 10, wherein the energy provided by said relatively high energy portion of each of said pulses is provided by spark discharge.

12. The method of claim 10, wherein the energy provided by said relatively high energy portion of each of said pulses is provided by laser.

13. The method of claim 9, wherein said relatively high energy poriton of each of said pulses includes a first relatively high peak while said relatively low energy portion includes a second peak which is lower and less steep than said first peak.

14. The method of claim 13, wherein said relatively low energy portion further includes a third peak which is lower and less steep than said second peak and continues from said second peak.

15. Apparatus for emission spectroscopic analysis of a sample containing elements to be analyzed, comprising:
means for providing energy in the form of cyclic pulses each having a waveform which comprises a relatively high energy portion which provides a sufficient amount of energy to vaporize said elements contained in said sample and a relatively low energy portion which continues from said high-energy portion and provides a sufficient amount of energy to cause said vaporized elements to emit light, and concentrating the energy of each of said pulses on said sample;
means for spectroscopically measuring the light emitted by said vaporized elements; and
means for controlling said light measuring means so that said light measuring means measures the light emitted by said vapor a predetermined period of time after the beginning of said relatively high energy portion of each of said pulses.

16. The apparatus of claim 15, wherein said energy providing and concentrating means comprises means for producing spark discharges.

17. The apparatus of claim 15, wherein said energy providing and concentrating means comprises a laser for producing a laser beam to be concentrated onto a required area of said sample to vaporize said elements contained therein and a spark geneator to generate a spark to cause said vaporized elements to emit light.

18. The apparatus of claim 15, wherein said controlling means controls said light measuring means so that the latter means measures the light emitted by said elements vaporized in the end portion of said high energy portion of each of said pulses as well as in said low energy portion thereof.

19. The apparatus of claim 15, wherein said relatively low energy portion of each of said pulses provides a sufficient amount of energy to cause said elements contained in said sample to vaporize and simultaneously emit light, and wherein said controlling means controls said light measuring means so that the latter means measures the light emitted by said elements vaporized only in said low energy portion of each of said pulses.

* * * * *